United States Patent

Hasegawa et al.

[11] Patent Number: 5,681,974
[45] Date of Patent: Oct. 28, 1997

[54] MO ADSORBENT FOR $^{99}$MO-$^{99M}$TC GENERATORS AND MANUFACTURING THEREOF

[75] Inventors: Yoshio Hasegawa; Mizuka Nishino; Taketoshi Takeuchi; Katsuyoshi Tatenuma; Masakazu Tanase; Kiyoyuki Kurosawa, all of Ibaraki-ken, Japan

[73] Assignees: Kaken Co., Ltd., Ibaraki-ken; Japan Atomic Energy Research Institute, Tokyo, both of Japan

[21] Appl. No.: 650,317

[22] Filed: May 20, 1996

[30] Foreign Application Priority Data

May 22, 1995 [JP] Japan .................. 7-146844

[51] Int. Cl.$^6$ .................. C07F 7/00; C07F 13/00; C08G 79/00
[52] U.S. Cl. .................. 556/54; 556/56; 534/14; 528/395
[58] Field of Search .................. 528/395, 394; 556/54, 56; 534/14

[56] References Cited

U.S. PATENT DOCUMENTS 4,524,201  6/1985  Barnabeo et al. .................. 528/395

FOREIGN PATENT DOCUMENTS 1129031  5/1989  Japan .
1129032  5/1989  Japan .
406157767  6/1994  Japan .

*Primary Examiner*—Porfirio Nazario-Gonzalez
*Attorney, Agent, or Firm*—Flynn, Thiel, Boutell & Tanis, P.C.

[57] ABSTRACT

Mo adsorbent for $^{99}$Mo-$^{99m}$Tc generators has a skeleton structure having mainly repeating units represented by the general formula;

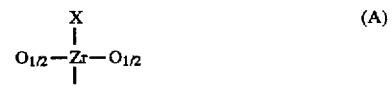

(A)

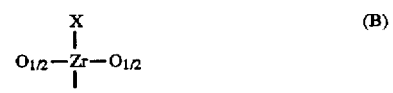

(B)

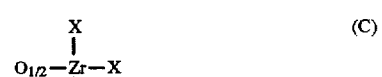

(C)

$$-R- \quad (D)$$

wherein X is a halogen atom or alkoxide group having one to six carbon atoms, 10% or more of X is halogen, R is an alkylene, polymethylene, or carbon chain having unsaturated bond, repeating unit (D) is bonded to any one of repeating units (A), (B), and (C), the branch structure is controlled by the content of repeating units (A), (B), and (C), the adsorbent is insoluble in water and adsorbs selectively only Mo from an aqueous solution containing Mo, and elutes $^{99m}$Tc generated from a radioactive isotope $^{99}$Mo. This Mo adsorbent uses $^{99}$Mo obtained from natural Mo by (n, γ) method, therefore, a generator having the same size as conventional $^{99m}$Tc generators is realized.

6 Claims, No Drawings

MO ADSORBENT FOR $^{99}$MO-$^{99m}$TC GENERATORS AND MANUFACTURING THEREOF

BACKGROUND OF THE INVENTION

1. Field of the Invention

This invention relates to Mo adsorbent for $^{99}$Mo-$^{99m}$Tc generators and manufacturing thereof for using $^{99m}$Tc for radiological diagnosis in the nuclear medical field.

2. Description of the Related Art $^{99m}$Tc has been used most popularly in the radiological field. $^{99m}$Tc is obtained as a daughter nuclide of $^{99}$Mo and has been mass-produced. For example, as presented in the commentary descriptions in Journal of Japan Atomic Energy Society (Shikata Eiji, Akira Iguchi, Journal of Japan Atomic Energy Society Vol. 26, No. 8 (1984) 662–670), $^{99m}$Tc is dosed to human body as a radiological agent for radiological diagnosis of cancer. However, for popularization of $^{99m}$Tc, the excellence in radiological and chemical characteristics, development of a generator, and progress of a diagnostic equipment are important. In detail, the half-life of $^{99m}$Tc is as short as 6.02 hours, and $^{99m}$Tc radiates only γ-ray, therefore, the prescription of $^{99m}$Tc results in only reduced human body exposure dose, and when a radioactive isotope is prescribed to a human body as a label to observe the distribution and behavior of the radioactive substance by measuring the radiation from the outside of the body, it is required for the radioactive isotope to have affinity with a target such as an organ or morbid tissue, to be cumulative, and to form a stable label substance by combining with other various substances. $^{99m}$Tc is excellent in these properties required for labeling.

Conventionally, two methods for retrieving $^{99m}$Tc from $^{99}$Mo, namely generator and solution type, have been used to use $^{99m}$Tc as a radioactive medical agent. The generator is an equipment which is a lead shielding container containing a column packed with alumina Mo adsorbent containing adsorbed $^{99}$Mo in a form of $MoO_4^{2-}$, only by charging sterilized physiological salt-water into the column, only $^{99m}$Tc generated from $^{99}$Mo is eluted in a form of $^{99m}TcO_4^-$. This operation is referred to as milking, and because $^{99}$Mo and $^{99m}$Tc reach radioactive equilibrium in a day, milking can be operated every day while $^{99}$Mo remains, various generators are available commercially. On the other hand, the solution type is supplied as a solution of a label substance synthesized by a process that $^{99m}$Tc is extracted from an aqueous solution containing $^{99}MoO_4^{2-}$ with a solvent such as methyl-ethyl-ketone, the solvent is evaporated to retrieve $^{99m}$Tc, then $^{99m}$Tc is used to synthesize various label substances. Therefore, a generator which does not require the extraction of $^{99m}$Tc with short half-life and operation for converting to a label substance is advantageous.

$^{99}$Mo is necessary to use $^{99m}$Tc, and two methods, one is (n, γ) method in which natural Mo is irradiated in a nuclear reactor and the other is nuclear fission (n, f) method in which $^{99}$Mo is retrieved from nuclear fission products of $^{235}$U, have been known. (n, γ) method is a method which utilizes $^{98}$Mo (n, γ) $^{99}$Mo reaction of Mo, involves a simple process, and involves only two radioactive substances of $^{99}$Mo and $^{99m}$Tc and easy radioactive shielding, and generates no radioactive waste, these characteristics favors this method.

However contrary to the above advantages, the natural abundance ratio of $^{98}$Mo is as low as 24.1%, and the specific activity of Mo obtained by (n, γ) method is as low as around 2 Ci/g, therefore, to get $^{99}$Mo in an amount of about 500 mCi necessary for a generator using alumina having an adsorptive capacity of as low as 2 mg/g, about 130 g of alumina is required. If 100% $^{98}$Mo is used, about 30 g of alumina is required, therefore, this method is not practical for use. By the reason described herein above, the generator of the nuclear fission (n, f) method is commercially used currently, which generator utilizes $^{99}$Mo with specific activity of as high as about $10^5$ Ci/g, is rendered small-sized and light weight, and does not have problems in handling, price, and transportation. However, in the nuclear fission method, fission reaction of $^{235}$U is utilized and $^{99}$Mo is retrieved from a mixture containing various nuclear fission products through complex processes, and the process generates much radioactive waste, such involvements are disadvantages of this method.

To cope with these disadvantages, a study to develop a generator having practical size which utilizes $^{99}$Mo generated by (n, γ) method has been conducted (J. V. Evans, P. W. Moore, M E. Shying and J. M. Sodeau, Appl.Radiat.Isot, vol.38, No.1 (1987) 19–23), and as the result, what is called gel generator is used practically in China. According to this method, $Na_2^{99}MoO_4$ prepared from $MoO_3$ by (n, γ) method is reacted with $ZrOCl_2$ or $ZrO(NO_3)_2$ to synthesize $ZrO^{99}MoO_4 \cdot xH_2O$ gel, then the gel is dried, ground, and packed in a column, thus $^{99m}$Tc can be eluted by milking.

However, this method is involved in problems such as difficulties in filtration of the gel and drying, and much break-through of Mo as a generator, and this method has yet many problems to be solved for practical use. To cope with the problems described above, Mo adsorbent with high Mo adsorptive capacity is required for the development of a practical generator utilizing (n, γ) method for obtaining $^{99}$Mo from natural Mo.

OBJECT AND SUMMARY OF THE INVENTION

It is the object of the present invention to obtain excellent Mo adsorbent to fabricate a practical generator having the same size as conventional $^{99m}$Tc generators using $^{99}$Mo prepared from natural Mo by (n, γ) method without the above-mentioned problems.

The inventors of the present invention have conducted a development work to achieve the above-mentioned object, as the result, succeeded in synthesis of zirconium-based inorganic polymer having excellent Mo adsorptive capacity and Tc elution, thus the present invention is accomplished.

Mo adsorbent for $^{99}$Mo-$^{99m}$Tc generators in accordance with the present invention has a skeleton structure having mainly repeating units represented by the formula;

$$O_{1/2}-\underset{\underset{X}{|}}{\overset{\overset{X}{|}}{Zr}}-O_{1/2} \quad (A)$$

$$-R- \quad (D)$$

wherein X is a halogen atom or an alkoxide group having one to six carbon atoms, 10% or more of X is halogen atoms, R is an alkylene, polymethylene, or charbon chain having unsaturated bonds with individually one to six carbon atoms, repeating unit (D) is bonded to any one of the repeating unit (A), (B), and (C), the branch structure is controlled by the content of the repeating unit (A), (B), and (C), the Mo adsorbent is insoluble in water, adsorbs only Mo selectively from an aqueous solution containing Mo, and elutes $^{99m}$Tc generated from radioactive isotope $^{99}$Mo.

A method for manufacturing Mo adsorbent for $^{99}$Mo-$^{99m}$Tc generators comprises the first step for reacting at least one of zirconium halide and zirconium oxide halide with an alcohol having one to six carbon atoms in solvent or without solvent, the second step for hydrolysis or coordination with water as required, and the third step for introducing cross-linking to the precursor obtained in the previous steps by heating in an oxidative or non-oxidative atmosphere containing moisture as required to render the product water-insoluble.

In the manufacturing method of Mo adsorbent for $^{99}$Mo-$^{99m}$Tc generators, a precursor generated by the reaction of starting material of zirconium halide or zirconium oxide halide with an alcohol is heat-treated, thereby, water-insoluble polymer is obtained. The water-insoluble polymer is rendered a Mo adsorptive capacity corresponding to the heat treatment temperature, therefore, the polymer is used as an adsorbent for adsorbing Mo from an aqueous solution of Mo. The Mo adsorbent synthesized as mentioned herein above is resistant to aging in dry state, adsorbs 60 mg or more, usually 200 mg or more per one gram of adsorbent, and elutes 80% or more of $^{99m}$Tc generated from $^{99}$Mo.

As described herein above, according to the present invention, Mo adsorbent for $^{99}$Mo-$^{99m}$Tc generators is manufactured utilizing $^{99}$Mo obtained from natural Mo or 100% $^{98}$Mo by (n, γ) method.

PREFERRED EMBODIMENTS OF THE INVENTION

Examples of the present invention will be described in detail hereinafter referring preferred embodiments and detailed examples.

First, an example of manufacturing method of Mo adsorbent for $^{99}$Mo-$^{99m}$Tc generators in accordance with the present invention is described herein under.

As the zirconium halide and zirconium oxide halide used in the first step of the manufacturing method, zirconium chloride is used preferably, especially $ZrCl_4$ is preferably used. Examples of the other starting material used as the alcohol having one to six carbon atoms include monohydric alcohols such as methanol, ethanol, isopropyl-alcohol, butanol, dihydric alcohols such as ethylene-glycol, and polyhydric alcohols such as glycerin and polyvinyl-alcohol. Though benzyl alcohol and phenol can be used as the starting material of Mo adsorbent of the present invention, the adsorptive capacity is low and they require a high heating temperature, therefore, these aromatic alcohols are disadvantageous because of low dissolution efficiency of $^{99m}$Tc. Therefore, the above-mentioned alcohols having one to six carbon atoms are preferably used.

The reaction in the first step can proceed without solvent, however, if the reaction product changes to a solid to cause concernedly heterogeneous reaction, an inert solvent such as tetrahydrofuran may be used for the reaction, otherwise, excessive amount of alcohol may be used to utilize unreacted alcohol as a solvent. Unreacted alcohol is served as a solvent because in the reaction of, for example, $ZrCl_4$ with excessive amount of alcohol ROH, $ZrCl_x(OR)_{4-x}$ is generated to leave chlorine required for Mo adsorption as described hereinafter. A reaction temperature in the first step may be a room temperature, but may be 150° C. or lower by heating to remove unreacted alcohol or solvent.

Subsequent to the first step, the second step may be applied as required for hydrolysis or coordination with water by addition of water. The purpose of the second step is to favor the following cross-linking between precursor in the third step by utilizing dehydration condensation reaction between hydroxyl groups generated by hydrolysis of alkoxide groups in the precursor generated in the first step or coordination of zirconium with water. A reaction temperature in the second step may be a room temperature, when alcohol generated by the hydrolysis, unreacted water, alcohol, and solvent are removed, the reaction mixture is heated to a temperature which is sufficient to evaporate.

The third step is a process to introduce cross-links to the precursor and increase the molecular weight involving a reaction such as dealcoholization, dehydration, dehydrocarbonization, and oxidation by heating in an oxidative atmosphere such as air and oxygen or a non-oxidative atmosphere such as nitrogen and argon. The heating temperature is in a temperature range from a reaction temperature of the first step or second step to 1000° C. The Mo adsorptive capacity of an adsorbent decreases rapidly beyond the reaction temperature of 700° C., and in the case that the reaction temperature of the first step or second step is 150° C. or lower, water soluble component remains occasionally in an adsorbent, therefore, the reaction temperature of the third step is preferably in a range from 150° C. to 700° C. The heat treatment at a temperature of 400° C. or higher can result in reduced elution efficiency of $^{99m}$Tc generation from $^{99}$Mo depending on the case, in such case, the heat treatment temperature should be 400° C. or lower. The heating time is preferably as short as possible as long as water-soluble component is cross-linked, though generally saying, the heating time is longer for a lower temperature and shorter for a higher temperature. In an atmosphere containing moisture, thermal decomposition reaction such as dealcoholization and dehydrocarbonization is accelerated by hydrolysis, such atmosphere allows the heat treatment temperature to be low, the low heat treatment temperature favors the manufacturing of adsorbent having high Mo adsorptive capacity. Water coordinated in the second step is more effective than water in the atmosphere.

Mo adsorbent for $^{99}$Mo-$^{99m}$Tc generators obtained as described herein above has a skeleton structure having mainly repeating units represented by the general formula;

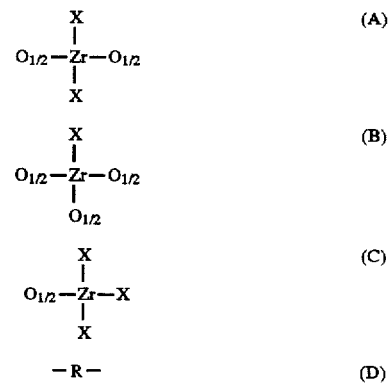

The repeating unit (C) forms the end of polymeric molecules of Mo adsorbent. The adsorbent is insoluble in water and organic solvents, therefore, molecular weight of the adsorbent is not measurable, based on this fact, the adsorbent is estimated to be a highly cross-linked polymer having scarce end groups. The adsorbent containing much repeating unit (B) has a structure containing much cross-linking and complex branching, and the content of repeating unit (D) can be 50% or more when a dihydric alcohol is used, but the content of repeating unit (D) is only 10% or less of the total units when usual monohydric alcohol is used, because repeating unit (D) is decomposed almost to leave only oxygen atoms bonded to Zr in the third step. The ratio of repeating unit (A) and (B) depends on the heat treatment temperature, the higher temperature results in increased ratio of repeating unit (B). On the other hand, the proportion of halogen atom in X of repeating unit (A), (B), and (C) is 10% to 80%, and the higher heat treatment temperature in the third step results in reduced proportion of halogen atom.

As described hereinbefore, starting material zirconium halide or zirconium oxide halide is reacted with an alcohol to yield a precursor, and the precursor is heat treated to form a water-insoluble polymer, and the water-insoluble polymer has Mo adsorptive capacity corresponding to the heat treatment temperature, therefor, the Mo adsorbent for $^{99}$Mo-$^{99m}$Tc generators described herein above in accordance with the present invention can be used as an adsorbent for adsorbing Mo from an aqueous solution of Mo. The synthesized adsorbent is resistant to aging in dry condition, adsorbs 60 mg or more, usually 200 mg or more of Mo per one gram of adsorbent, elutes 80% or more of $^{99m}$Tc generated from $^{99}$Mo, thus the Mo adsorbent brings the possibility of manufacturing of a generator utilizing $^{99}$Mo obtained from natural Mo and 100% $^{98}$Mo by (n, γ) method.

The reason of the effect of the Mo adsorbent for $^{99}$Mo-$^{99m}$Tc generators in accordance with the present invention is attributed mainly to the formation of bonding between Zr atoms by heat treatment of the precursor yielded through the reaction between a zirconium compound and an alcohol. Because of the insolubility in water due to the conversion to polymeric substance by branching, the conversion to polymeric substance in the presence of much residual chlorine atoms in the precursor, and the conversion of Zr in polymer chain to cations by hydrolyzing residual chlorine atoms in an aqueous solution, it is estimated that the Mo adsorbent can adsorb Mo ions in ionic mode.

As shown in a comparative example of the following examples described hereinafter, the inorganic substance obtained by hydrolysis of ZrCl$_4$ followed by heat treatment is scarcely effective, this fact validates the above-mentioned reasons.

The Mo adsorption mechanism of the Mo adsorbent for $^{99}$Mo-$^{99m}$Tc generators of the present invention is estimated to involve the chemical bonding of MoO$_4^{2-}$ to Zr is shown herein under.

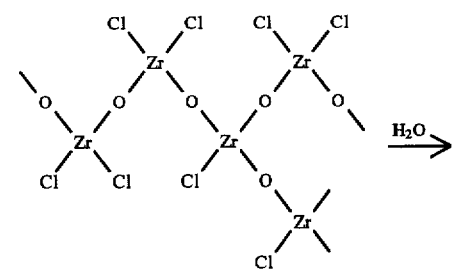

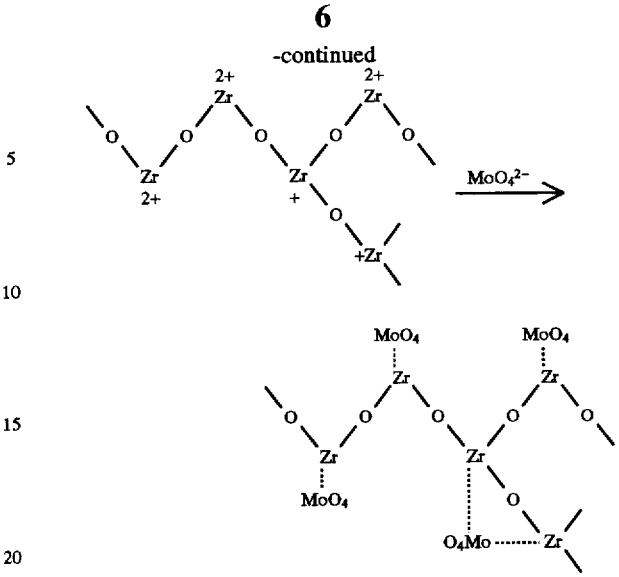

Of course, the effect of the invention is by no means limited by this mechanism, and other mechanisms may be possible. It is estimated that the replacement of $^{99}$Mo chemically combined to Zr with $^{99m}$Tc allows $^{99m}$Tc having weak bonding to Zr to be eluted in a form of $^{99m}$TcO$_4^-$.

Next, a detailed example in accordance with the present invention is described herein under.

A 500 ml three-neck flask was equipped with a stirrer, dry nitrogen gas inlet tube, and thermometer, the internal of the flask was filled with nitrogen gas, 46.6 g of ZrCl$_4$ (0.2 mol), and prescribed ratio of ethanol, isopropanol, butanol, ethyleneglycol, glycerin, or polyvinyl-alcohol, and a solvent as required were added into the flask, and the mixture was reacted at a room temperature with stirring. The reaction started immediately and the temperature of the mixture rose to about 50° C. and then cooled gradually. Then, a prescribed amount of water was added as required, and the mixture was heated to a prescribed temperature to synthesize a precursor of the Mo adsorbent. Then, the precursor was heat treated in any one of atmospheres of air, argon gas, and oxygen gas to synthesize the Mo adsorbent. Alcohols used for the preparation of adsorbents and conditions applied in the first and the second steps are listed in Table 1, and conditions applied in the third step is listed in Table 2. As comparative examples, comparative substances were synthesized from ZrCl$_4$ and water as listed in Table 1 and Table 2.

The synthesized Mo adsorbents were subjected to Mo adsorption test using an aqueous solution of sodium molybdate having the specific activity of 14.8 mCi ($^{99}$Mo)/g(Mo) obtained by (n, γ) method, Mo adsorption per one gram of Mo adsorbent and the elution efficiency of $^{99m}$Tc were measured, and the result is listed in Table 2. For adsorption of Mo, one gram of Mo adsorbent was mixed with the aqueous solution of sodium bolybdate, the solution was kept at a room temperature or 90° C. until saturation of the adsorption, after reaching the radioactive equilibrium by standing one day, the milking operation was carried out using physiological aqueous solution of solt, and the elution efficiency of $^{99m}$Tc was measured. The Mo adsorption and elution efficiency of $^{99m}$Tc of the comparative samples were also measured, and the results are listed in Table 2.

Mo adsorption reaches the saturation about 18 hours at a room temperature and about 2 hours at 90° C. There is no difference between samples, all samples show almost the same value. 80% or more of $^{99m}$Tc is eluted by about 10 moles of physiological aqueous solution of salt. Contrary to these samples, the inorganic substances obtained from $ZrCl_4$ and water as shown in Table 1 and Table 2 as comparative examples did not present the characteristics as Mo adsorbent.

Mo adsorbents in accordance with the present invention presented stable $^{99m}Tc$ elution also in subsequent milking operations, it is proved that these Mo adsorbents are used as a generator.

TABLE 1

| | | alcohol | first step | | second step | |
|---|---|---|---|---|---|---|
| No | | (molar ratio to $ZrCl_4$) | solvent | temperature (°C.) | water content (molar ratio to $ZrCl_4$) | temperature (°C.) |
| 1 | | ethanol (2.0) | none | 90 | none | — |
| 2 | | ethanol (2.0) | THF | room temperature | 1.0 | 110 |
| 3 | | isopropyl alcohol (2.0) | none | 90 | none | — |
| 4 | | isopropyl alcohol (2.0) | THF | — | 1.0 | 90 |
| 5 | | isopropyl alcohol (1.8) | none | 90 | none | — |
| 6 | | isopropyl alcohol (1.0) | $CCl_4$ | 90 | none | — |
| 7 | | isopropyl alcohol (1.0) | THF | — | 1.0 | 90 |
| 8 | | butanol (1.0) | THF | — | 2.0 | 150 |
| 9 | | ethyleneglycol (1.0) | THF | 120 | none | — |
| 10 | | glycerin (½) | THF | 120 | none | — |
| 11 | | polyvinyl alcohol (1.0 in monomer unit) | water | 150 | — | — |
| comparative example | | none | water | 120 | — | — |

TABLE 2

| | | third step | | | Mo absorptive | Tc elution |
|---|---|---|---|---|---|---|
| No | atmosphere | temperature (°C.) | time (minutes) | water soluble percentage (%) | capacity (mg/g) | efficiency (%) |
| 1 | air | 220 | 0.5 | 10 | 220 | 90 |
| | | 230 | 0.5 | 0 | 200 | 85 |
| 2 | air | 200 | 0.5 | 10 | — | — |
| | | 210 | 30 | 0 | 180 | 82 |
| 3 | air | 200 | 0.5 | 1 | 250 | 93 |
| | | 210 | 0.5 | 0 | 230 | 85 |
| | | | 5 | 0 | 210 | 80 |
| | Ar | 205 | 60 | 0 | 210 | 81 |
| 4 | air | 160 | 30 | 0 | 270 | 93 |
| | | 180 | 30 | 0 | 190 | 91 |
| | | 200 | 0.5 | 0 | 160 | 88 |
| | | | 30 | 0 | 60 | 86 |
| 5 | Ar | 205 | 60 | 2 | 260 | 90 |
| | air | 210 | 0.5 | 10 | 200 | 87 |
| | | | 5 | 0 | 60 | 80 |
| 6 | Ar | 205 | 60 | 20 | — | — |
| 7 | air | 200 | 30 | 20 | — | — |
| | | 250 | 30 | 0 | — | — |
| 8 | $O_2$ | 280 | 10 | 5 | — | — |
| 9 | Ar | 300 | 60 | 2 | 215 | 79 |
| | | 325 | 60 | 0 | 150 | 75 |
| | | 500 | 60 | 0 | 60 | 13 |
| | air | 300 | 0.5 | 0 | 190 | 81 |
| 10 | Ar | 300 | 60 | 10 | 200 | 80 |
| | | 350 | 60 | 1 | 190 | 42 |
| | | 500 | 60 | 0 | 65 | 5 |
| 11 | Ar | 200 | 60 | 3 | 30 | 82 |
| | | 500 | 60 | 0 | 60 | 21 |
| comparative example | Ar | 200 | 60 | 98 | — | — |
| | | 250 | 60 | 0 | 8 | — |

What is claimed is:

1. Mo adsorbent for $^{99}$Mo-$^{99m}$Tc generators having a skeleton structure having mainly repeating units (A), (B), (C), and (D) represented by the general formula;

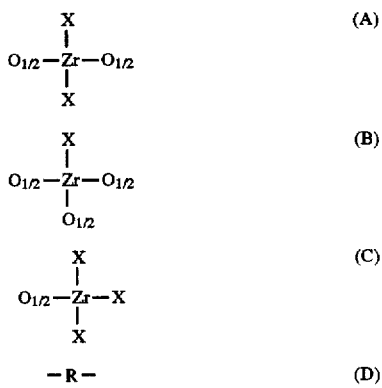

(A)
(B)
(C)
(D)

wherein X is a halogen atom or alkoxide group, R is an alkylene, polymethylene, or carbon chain having unsaturated bond, repeating unit (D) is bonded to any one of repeating units (A), (B), and (C), the branch structure is controlled by the content of repeating units (A), (B), and (C), said adsorbent is insoluble in water, adsorbs selectively only Mo from an aqueous solution containing Mo, and elutes $^{99m}$Tc generated from a radioisotope $^{99}$Mo.

2. Mo adsorbent for $^{99}$Mo-$^{99m}$Tc generators as claimed in claim 1, wherein 10% or more of X is halogen.

3. Mo adsorbent for $^{99}$Mo-$^{99m}$Tc generators as claimed in claim 1, wherein alkoxide group represented by X has one to six carbon atoms.

4. Mo adsorbent for $^{99}$Mo-$^{99m}$Tc generators as claimed in claim 1, wherein R is alkylene, polymethylene, or carbon chain having unsaturated bond and has one to six carbon atoms.

5. A method for manufacturing of Mo adsorbent for $^{99}$Mo-$^{99m}$Tc generators comprising the first step for reacting at least one of zirconium halide and zirconium oxide halide with an alcohol in a solvent or without solvent, the second step for hydration or coordinating with water as required, and the third step for cross-linking the precursor obtained as described herein above by heating in an oxidative or non-oxidative atmosphere containing moisture as required to render said Mo adsorbent insoluble in water.

6. A method for manufacturing of Mo adsorbent for $^{99}$Mo-$^{99m}$Tc generators as claimed in claim 5, wherein said alcohol used for the reaction in the first step has one to six carbon atoms.

* * * * *